US010945757B2

(12) United States Patent
Gurm et al.

(10) Patent No.: US 10,945,757 B2
(45) Date of Patent: Mar. 16, 2021

(54) TWO-PHASE TECHNIQUE TO RESTORE ARTERY PATENCY AND A CATHETER TEMPERATURE CONTROL SYSTEM IN ATHERECTOMY (71) Applicant: THE REGENTS OF THE UNIVERSITY OF MICHIGAN, Ann Arbor, MI (US)

(72) Inventors: Hitinder S. Gurm, Ann Arbor, MI (US); Yao Liu, Ann Arbor, MI (US); Yang Liu, Ann Arbor, MI (US); Yihao Zheng, Ann Arbor, MI (US); Albert Shih, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 145 days.

(21) Appl. No.: 16/342,573

(22) PCT Filed: Oct. 17, 2017

(86) PCT No.: PCT/US2017/057022
§ 371 (c)(1),
(2) Date: Apr. 17, 2019

(87) PCT Pub. No.: WO2018/075545
PCT Pub. Date: Apr. 26, 2018

(65) Prior Publication Data
US 2019/0262035 A1     Aug. 29, 2019

Related U.S. Application Data (60) Provisional application No. 62/409,410, filed on Oct. 18, 2016.

(51) Int. Cl.
A61B 17/3207     (2006.01)
A61B 17/00       (2006.01)
A61B 17/32       (2006.01)

(52) U.S. Cl.
CPC .............. A61B 17/320758 (2013.01); *A61B 2017/00084* (2013.01); *A61B 2017/00092* (2013.01);
(Continued)

(58) Field of Classification Search
CPC ........ A61B 17/320758; A61B 17/3207; A61B 2217/007; A61B 2017/00084;
(Continued)

(56) References Cited

U.S. PATENT DOCUMENTS

2009/0024085 A1* 1/2009 To ................... A61B 17/320758
                                                      604/95.01
2009/0306691 A1  12/2009 Cambronne et al.
(Continued)

FOREIGN PATENT DOCUMENTS

WO    WO-2010132147 A1    11/2010

OTHER PUBLICATIONS

Shih, Albert J. et al., "Grinding wheel motion, force, temperature, and material removal in rotational atherectomy of calcified plaque", CIRP Annals—Manufacturing Technology, Jan. 7, 2016 (online), vol. 65, Issue 1, pp. 345-348.
(Continued)

*Primary Examiner* — Kathleen S Holwerda
*Assistant Examiner* — Brooke Labranche
(74) *Attorney, Agent, or Firm* — Harness, Dickey & Pierce, P.L.C.

(57)     ABSTRACT

A method of two-phase atherectomy for removal of plaque within an artery forming a stenosis including a first phase of rotational drilling by exerting a rotational force on a cutter
(Continued)

to form a channel within the plaque having a diameter substantially equal to a diameter of the cutter—the cutter being rotated at a first rotational speed sufficient to maintain rotation of the cutter about a stationary rotational axis—and a second phase of orbital impact by exerting a rotational force on the cutter to result in radial orbital motion of the cutter within the channel resulting in periodic impact of the cutter upon the plaque to form micro-fractures within the plaque and enlarge the diameter of the channel to a diameter substantially greater than the diameter of the cutter—the cutter being rotated at a second rotational speed to result in the radial orbital motion of the cutter.

13 Claims, 12 Drawing Sheets

(52) U.S. Cl.
CPC .............. *A61B 2017/320004* (2013.01); *A61B 2017/320766* (2013.01); *A61B 2217/007* (2013.01)

(58) Field of Classification Search
CPC ......... A61B 2017/00092; A61B 2017/320004; A61B 2017/320766
See application file for complete search history.

(56) References Cited

U.S. PATENT DOCUMENTS

| | | |
|---|---|---|
| 2010/0100110 A1 | 4/2010 | Cambronne et al. |
| 2010/0121361 A1 | 5/2010 | Plowe et al. |
| 2010/0198239 A1* | 8/2010 | McBroom ...... A61B 17/320758 606/159 |

OTHER PUBLICATIONS

International Search Report and Written Opinion for PCT/US2017/057022, dated Jan. 31, 2018; ISA/KR.

* cited by examiner

TWO-PHASE TECHNIQUE TO RESTORE ARTERY PATENCY AND A CATHETER TEMPERATURE CONTROL SYSTEM IN ATHERECTOMY

CROSS-REFERENCE TO RELATED APPLICATIONS

This application is a U.S. National Phase Application under 35 U.S.C. 371 of International Application No. PCT/US2017/057022 filed on Oct. 17, 2017, which claims the benefit of U.S. Provisional Application No. 62/409,410, filed on Oct. 18, 2016. The entire disclosures of the above applications are incorporated herein by reference.

GOVERNMENT INTEREST

This invention was made with government support under CMMI1232655, awarded by the National Science Foundation. The Government has certain rights in the invention.

FIELD

The present disclosure relates to a two-phase technique to restore artery patency and a catheter temperature control system in atherectomy.

BACKGROUND AND SUMMARY

This section provides background information related to the present disclosure which is not necessarily prior art. This section provides a general summary of the disclosure, and is not a comprehensive disclosure of its full scope or all of its features.

Cardiovascular disease is the main cause of morbidity and mortality worldwide and it is predominantly caused by atherosclerosis. To treat cardiovascular diseases, atherectomy, an endovascular surgery, utilizes a cutter on a catheter to remove the calcified atherosclerotic plaque from the artery and restore the blood flow. With current atherectomy techniques and devices, complications including restenosis (regrowth of plaque), dissection, and slow-flow/no-reflow occur frequently. These complications are mainly caused by excessive cutting force and heat during atherectomy. Proper selection of the cutting speed and real-time temperature monitor and control will help to reduce the complication rates.

According to the principles of the present teachings, a two-phase atherectomy technique is provided to restore the artery patency with minimized cutting force and temperature rise. To assist this technique, a catheter temperature control system is optionally provided to avoid tissue thermal damage and blood coagulation.

In some embodiments, the two-phase atherectomy technique consists of Phase I—low-speed rotational drilling and Phase II—high-speed orbital impact resulting in plaque micro-fractures. During Phase I, when the lesion lumen size is smaller than the cutter, the rotating cutter advances through the stenosis and cuts the plaque off as a drill bit to create a channel of the cutter size. This process involves a large contact area between the cutter and plaque which tends to cause high cutting force and temperature. Accordingly, low cutter rotational speed is required to avoid tissue damage. When the lumen size is enlarged to allow the cutter translation in the radial direction, the cutter orbits around the vessel due to blood fluid mechanics. While orbiting, the cutter hits the plaque, bounces up or away due to the cutting force, and is pushed to hit the plaque again by the centrifugal force. This process generates impact crater points and cracks in the plaque, further enlarging the lumen and disrupting the plaque tissue to restore artery patency and elasticity. The orbital and jumping motion are dominated by the orbital centrifugal force. To increase the orbital speed and impact force, high cutter rotational speed is recommended, as derived from our cutter motion study. As higher speeds are associated with a higher temperature and increased risk of blood coagulation and thermal injury, temperature control during atherectomy is imperative.

In some embodiments, catheter temperature control system comprises a sheath with a temperature sensor and a temperature regulator. The sheath is a plastic tube in which drive shaft rotates and saline flows. The shaft rotation on the guidewire generates heat. Saline (or other lubricant) flows to cool and lubricate the drive shaft. The temperature sensor, such as a thermocouple, is imbedded in the wall of the sheath along the catheter with the sensing probe locating near the treatment site. Real-time temperature during atherectomy is measured as the feedback signal to the temperature regulator. The regulator controls the lesion temperature by adjusting the level of cold water in a tank where saline flows through a section of coiled tube. When the cold water level rises, contact area for heat exchange between the cold water and the coiled tube increases and the saline temperature drops.

In some embodiments, there is no thermocouple but based on the rotational velocity elected for use, the temperature rise is estimated and the lubricant is cooled to a temperature sufficient to neutralize the heat generated in the catheter and prevent thermal injury to the vessel wall or to the flowing cells, proteins, and other constituents of blood in the vessel. In this embodiment, as the rotational speed is adjusted, this will trigger a change in the temperature of the coolant and thus of the lubricant and reduce tissue injury.

The clinical utility of this device would be to use the drilling phase to create a lumen that allows either large enough lumen to permit enough blood flow for relief of symptoms or for delivery of other interventional devices (especially drug eluting balloons or stents). The impact phase of the device will be used to create micro-fractures in the plaque that would then make the calcified plaque suitable for further intervention by high pressure balloon angioplasty or stenting and would respond appropriately to such devices. Thus the device would be used to prepare the lesion prior to stenting. This phase could also be applied for treatment of lesions where a stent is deployed but fails to fully expand and thus is at high risk for thrombosis and restenosis. The ability of the device to induce micro-fractures could thus be applied inside an incompletely expanded stent where the force transmitted at the impact craters could create plaque fissure points that could subsequently be expanded using a high pressure balloon or another device.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

BACKGROUND

Cardiovascular disease is the main cause of morbidity and mortality worldwide and it is predominantly caused by atherosclerosis, the accumulation of fatty and calcified materials (also known as plaque) on the arterial wall restricting blood flow. To treat cardiovascular diseases, atherectomy, an interventional cardiology procedure, removes the calcified plaque from the vessel wall to restore the blood flow, via a specialized catheter equipped with a grinding wheel to pulverize the plaque into fine debris inside the artery.

Figure 1A:
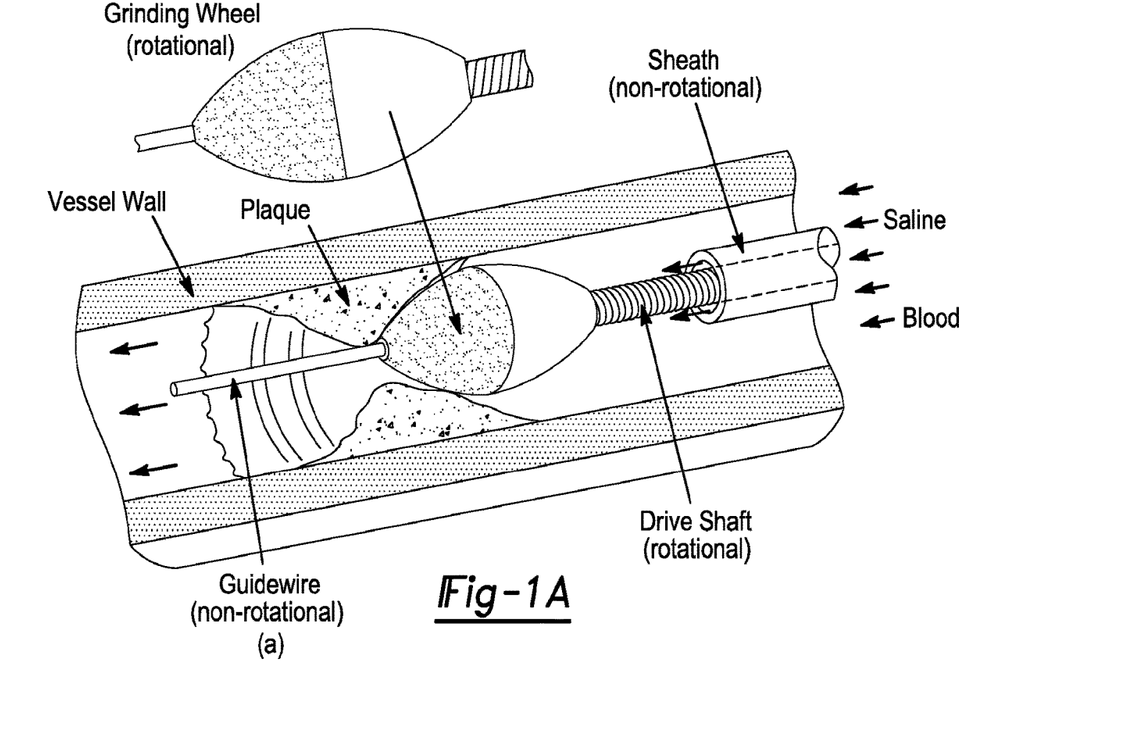
FIG. 1A illustrates grinding-based atherectomy devices using Rotablator™ rotational atherectomy.
Figure 1B:
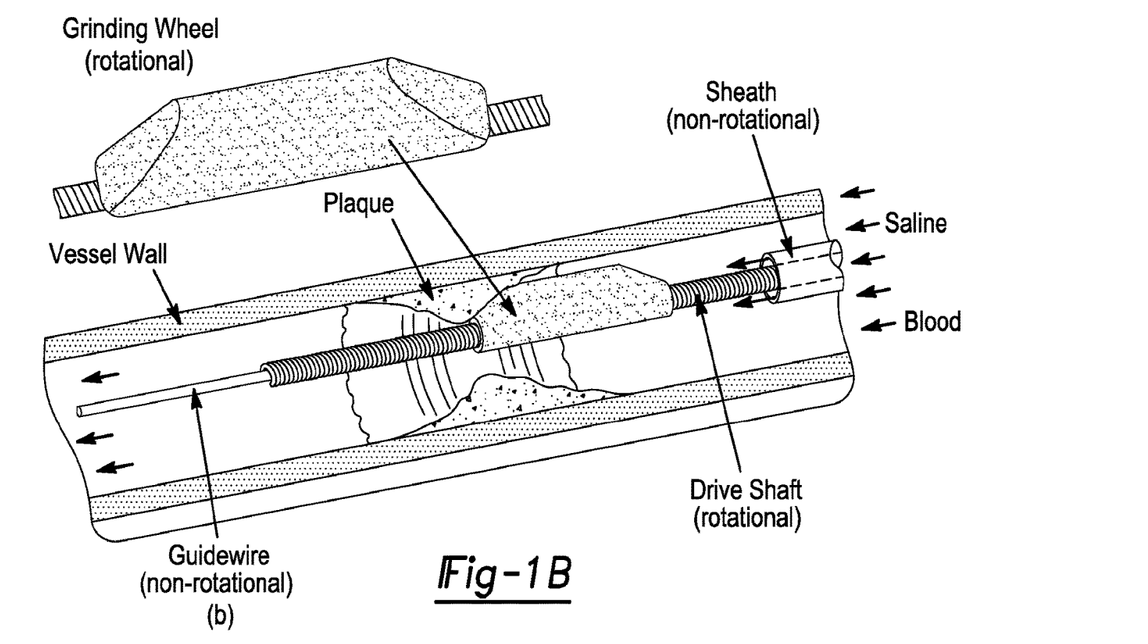
FIG. 1B illustrates grinding-based atherectomy devices using Diamondback 360® orbital atherectomy.

Two commonly used atherectomy devices are ROTABLATOR rotational atherectomy (RA) by Boston Scientific (Natick, Mass.) and Diamondback 360® orbital atherectomy (OA) by Cardiovascular System Inc. (Saint Paul, Minn.). These two devices, as shown in FIGS. 1A and 1B, respectively, share a similar mechanism of action. Specifically, a high-speed rotating grinding wheel, driven by a flexible drive shaft, translates along a non-rotational guidewire through the lesion to sand the plaque. The rotating drive shaft is contained in a non-rotational plastic sheath where saline is infused to provide cooling and lubrication. Blood flows outside the sheath and carries the debris into the human circulation system.

Grinding wheel geometry is the major difference between these two devices: an axisymmetric prolate spheroid with half abrasive coating is used in rotational atherectomy (FIG. 1A) and a wedged cylinder off-centered mounted on the drive shaft is used in orbital atherectomy (FIG. 1B). Clinically, the grinding wheels are commonly known as burr and crown for RA and OA, respectively.

Atherectomy techniques, including the selection of grinding wheel speed and size, are different in RA and OA.

Grinding Wheel Speed.

In RA, the wheel speed can be adjusted to any value between 50,000 and 230,000 rpm. However, there is currently no guideline for RA rotational speed. Clinical studies recommended a rotational speed range of 140,000 to 160,000 rpm, which is considerably below the device's top speed of 230,000 rpm. A European review suggested a wider range of 135,000 to 180,000 rpm for RA. A few later clinical studies utilized rotational speeds over 200,000 rpm.

On the other hand, OA has only two options of rotational speed in coronary atherectomy: low (80,000 rpm) or high (120,000 rpm) and it is specified in the OA instruction for use that initial treatment for each lesion must start at low speed. The lumen will be further enlarged using the high speed due to the increase of the centrifugal force of the eccentric design of the grinding wheel (FIG. 1B).

Grinding Wheel Size.

In RA, the grinding wheel diameter ranges from 1.25 to 2.5 mm at 0.25 mm increment. There is again confusion in RA wheel size selection in clinical studies: Tomey et al. found the use of a single burr with a burr-to-artery diameter ratio (B/A ratio) from 0.5 to 0.6 to be optimal. Barbato et al. suggested using multiple burrs by stepping up the size from 1.25 to 1.5 and then to 1.75 mm. Two randomized trials showed a B/A ratio smaller than 0.7 was beneficial with lower complication rates. For coronary OA, the grinding wheel has only one size, 1.25 mm diameter.

With current atherectomy devices and techniques, complications including restenosis (regrowth of plaque), dissection, and slow-flow/no-reflow occur frequently. These complications are mainly caused by excessive cutting force and heat during atherectomy. Proper selection of the cutting speed and grinding wheel size and real-time temperature monitor and control will help to reduce the complication rates.

Technology

In our research we have investigated the grinding wheel motion, force, resultant debris size and temperature rise, and challenges associated with these devices and provide the following.

Crown Dynamics in OA

Crown Motion

Figure 2A:
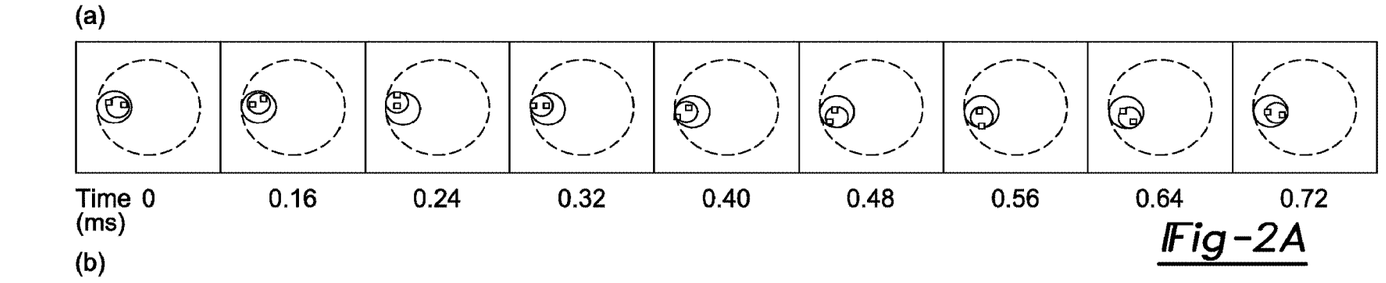
FIG. 2A illustrates the crown rotation and orbiting one rotational cycle.
Figure 2B:
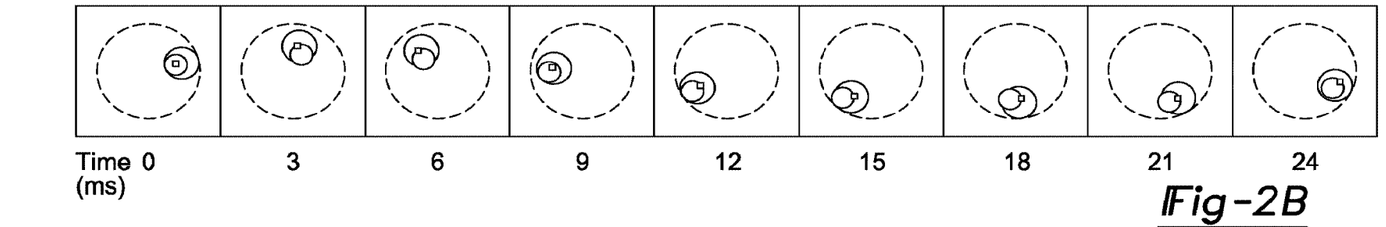
FIG. 2B illustrates the crown rotation and orbiting one orbital cycle observed by high-speed camera in axial direction when the crown rotates at 90,000 rpm.
Figure 2C:
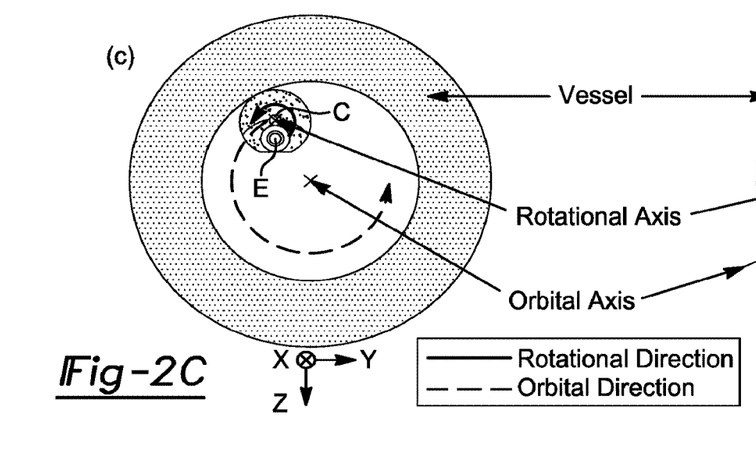
FIG. 2C is the front schematic view of the crown rotation and orbiting.
Figure 2D:
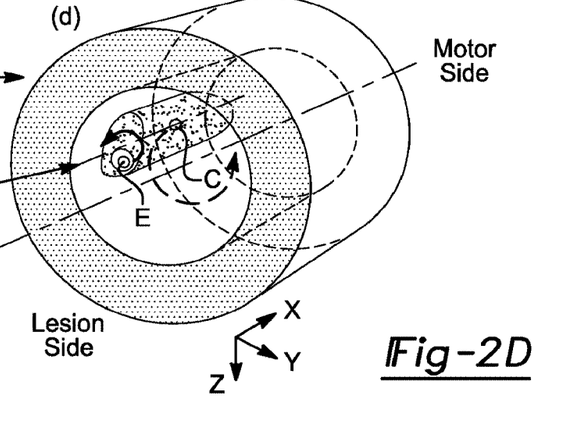
FIG. 2D is the perspective schematic view of the crown rotation and orbiting.
Figure 3A:
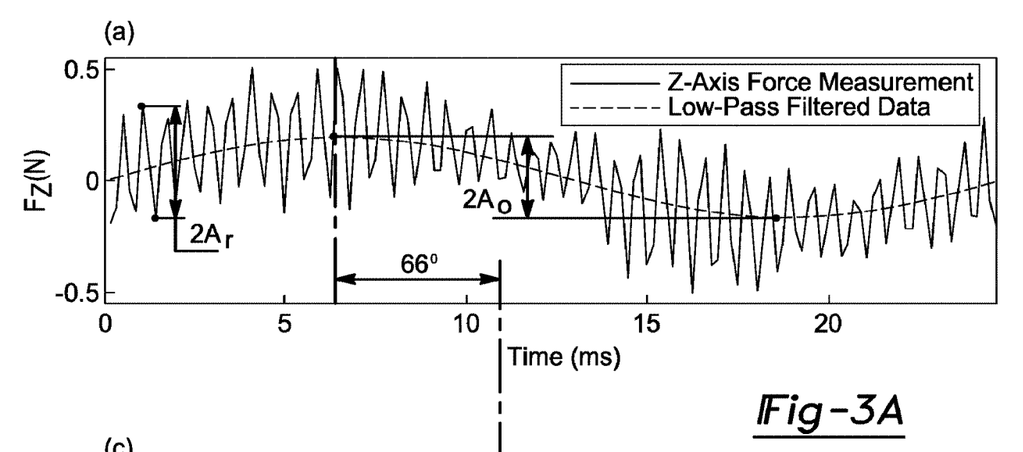
FIGS. 3A and 3B are graphs illustrating force measurements at 90,000 rpm crown rotational speed $F_Z$ in the time and frequency domains, respectively.
Figure 3B:
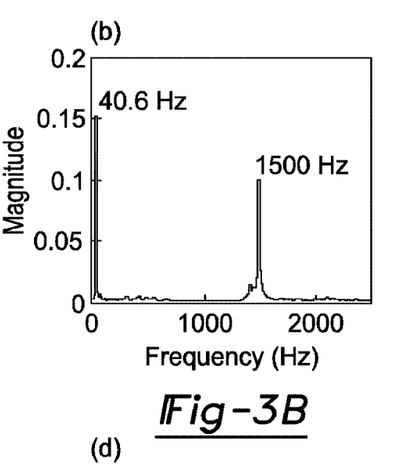
Figure 3C:
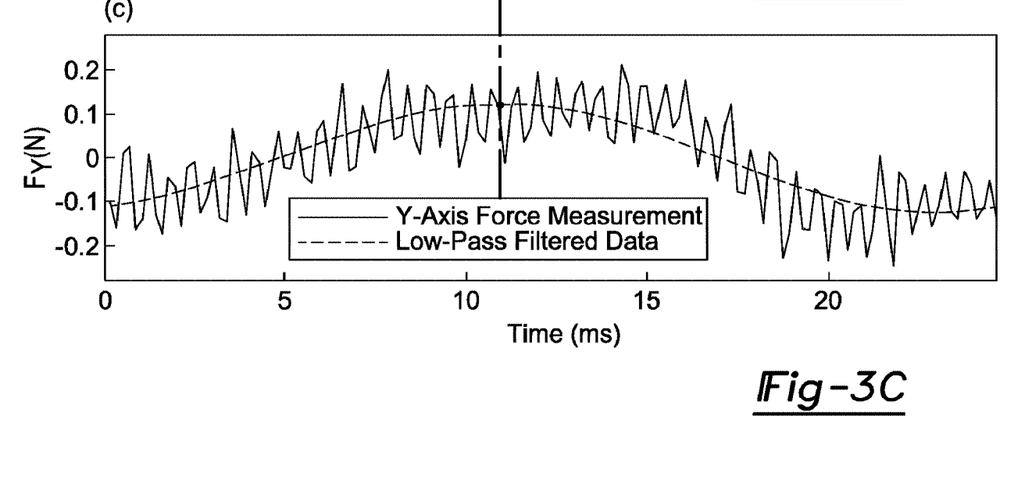
FIGS. 3C and 3D are graphs illustrating force measurements at 90,000 rpm crown rotational speed $F_y$ in the time and frequency domains, respectively.
Figure 3D:
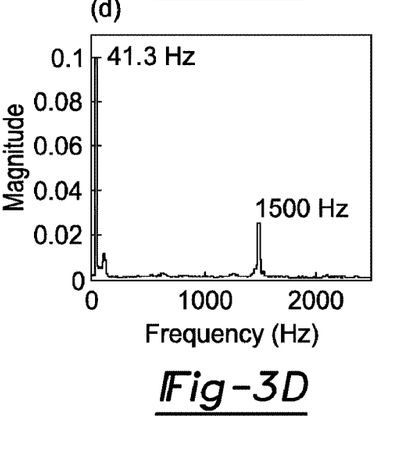

FIGS. 2A and 2B show the crown motion captured with a high-speed camera aimed along a vessel axis. FIG. 2A traces a cycle of crown rotation in 0.72 ms when crown connection point E completed one circle counterclockwise around its center point C. The crown rotated about its cylindrical axis and moved smoothly (no high-frequency C motion in FIG. 2D) against the vessel. FIG. 2B demonstrates a cycle of the crown orbiting to be about 24 ms with C traveling around the vessel lumen counterclockwise. The rotational and orbital directions of the crown were observed to be the same. To summarize, the high speed camera observation of the crown rotation and orbiting, two schematic views are presented in FIGS. 2C and 2D. The orbital speeds increase with the crown rotational speeds.

Contact Force

FIG. 3 shows the measured force in the Z- ($F_Z$) and Y-direction ($F_Y$) for one orbital period (24.4 ms) at the 90,000 rpm crown rotational speed. The combination of high and low frequencies was clearly seen in FIGS. 3A and 3C. The two dominant frequencies obtained from the FFT were 1,500 and 40.6 Hz for $F_Z$ and 1,500 and 41.3 Hz for $F_Y$ as shown in FIGS. 3B and 3D, respectively.

The crown orbital motion could reduce the heat accumulation and tissue thermal injury. Abrasive sanding is an energy intensive process and its accompanying heat, if accumulated, can cause blood coagulation and tissue thermal injury during atherectomy. The combination of rotational and orbital motions of the crown avoids any continuous contact between a specific region of the vessel and the rotating crown allows continuous blood flow. Such characteristic behavior of the crown motion could be exploited to aid in heat dispersion making orbital atherectomy safer with respect to thermal injury to the artery wall.

Cyclic loading on the vessel in orbital atherectomy could soften the plaque tissue. Stress softening of atherosclerotic plaque is similar to the Mullins effect in rubber. In orbital atherectomy, the plaque undergoes cyclic loading due to the crown's orbital motion. The crown rotational motion contributes additional cyclic loading, elevating the local stress and further enhancing the stress softening. This pulsatile force into the tissue may increase the compliance of the lesion, facilitating higher rates of success in angioplasty and stenting, as was observed in clinical trials.

Burr Dynamics in RA

Burr Motion

An orbital motion of the burr around the arterial wall was observed as illustrated in FIG. 4. Five video images with 2.9 ms time step in the radial and axial directions are shown in FIGS. 4A and 4B, respectively. The burr orbits around the vessel at 5,170 rpm, much lower than the 160,000 rpm rotational speed. The burr motion in RA is illustrated schematically in FIG. 4C. The burr rotational and orbital directions are the same. The burr rotates about its axis (at 160,000 rpm) and orbits about the vessel axis (at 5,170 rpm). To our knowledge, this observation of burr motion in RA has not yet been reported in the literature. The grinding zone orbits around the vessel. The burr orbiting motion enables a small diameter burr grinding a large diameter vessel and enhances the heat dissipation from the grinding zone.

Figure 4A:
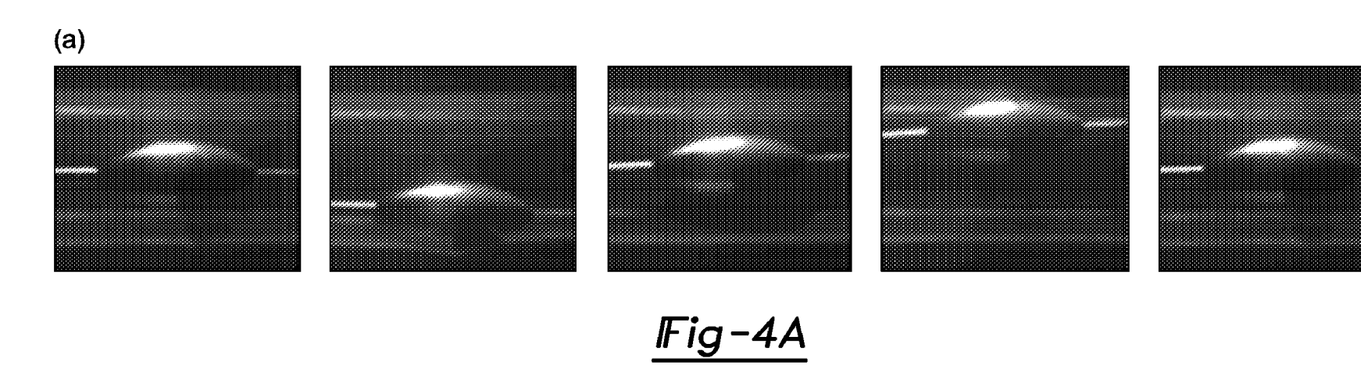
FIG. 4A illustrates the Burr (grinding wheel) motion in radial directions.
Figure 4B:
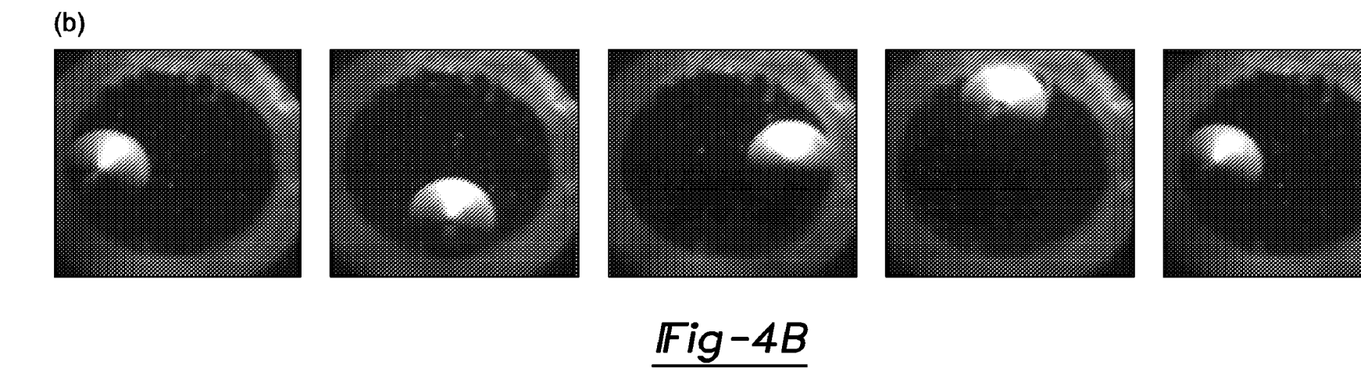
FIG. 4B illustrates the Burr (grinding wheel) motion in axial-directions.
Figure 4C:
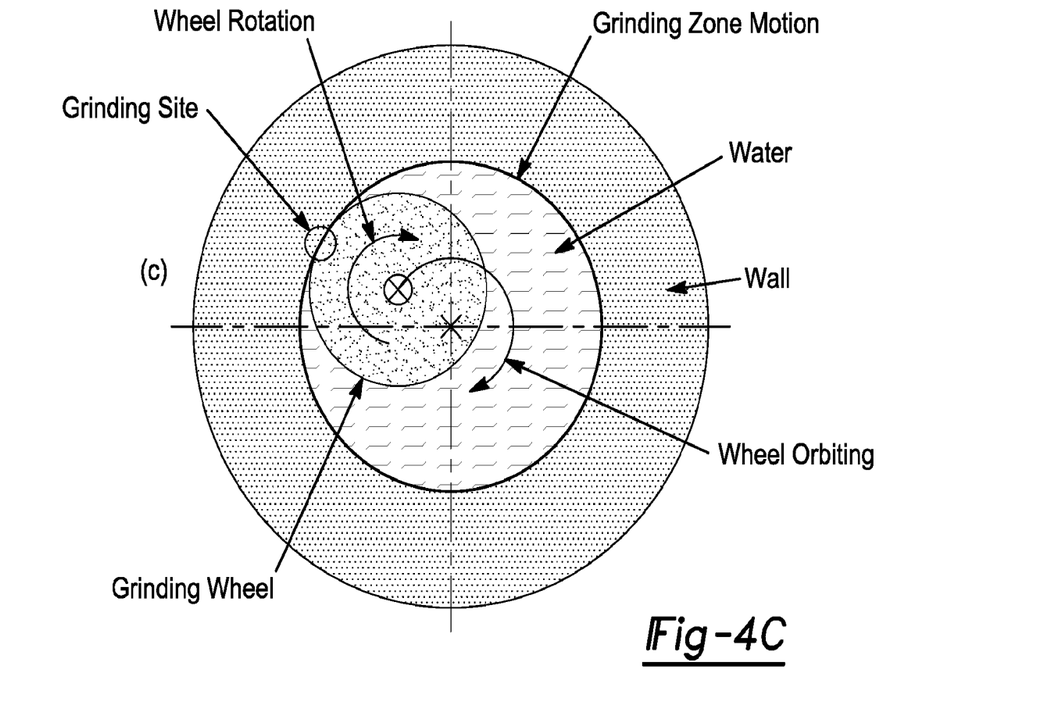
FIG. 4C is a schematic of the burr motion in rotational atherectomy (RA).
Figure 4D:
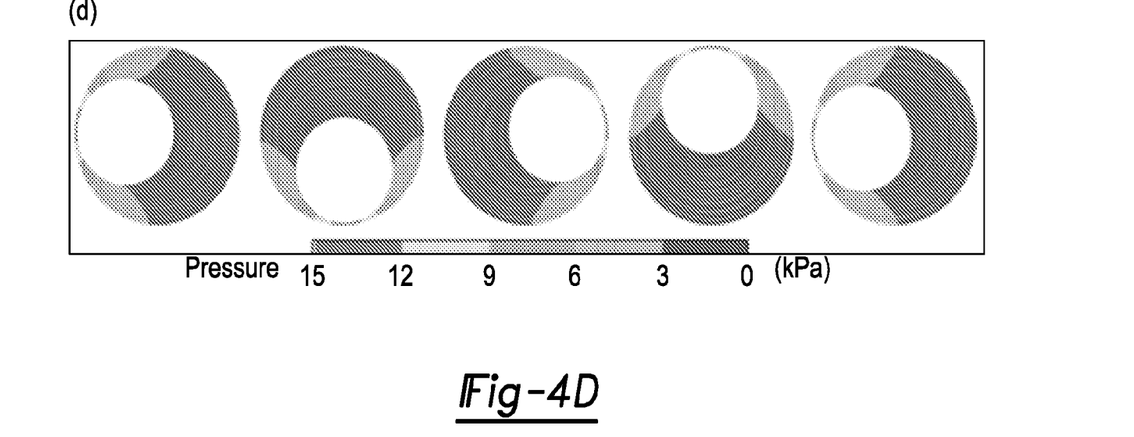
FIG. 4D shows the CFD simulation results.

Similar to a hydrodynamic bearing, we believe the burr orbital motion is created by a fluid pressure film between the burr and vessel. A computational fluid dynamics (CFD) simulation was conducted in ANSYS Fluent 15.0. The rotation of the burr induces a flow that lifts and orbits the burr. The pressure distribution and streamline in five positions of an orbital period are shown in FIG. 4D. The orbital direction matches the motion observed in FIGS. 4A and 4B.

The orbital motion in RA has been largely ignored in clinical practice. A burr with a diameter larger than that of the lesion lumen was typically chosen to "drill" through the lesion, which may lead to excessive grinding forces and heat generation. This study suggests a burr much smaller than the lumen size is capable of orbiting and still grinding the plaque.

Grinding Force

Figure 5A:
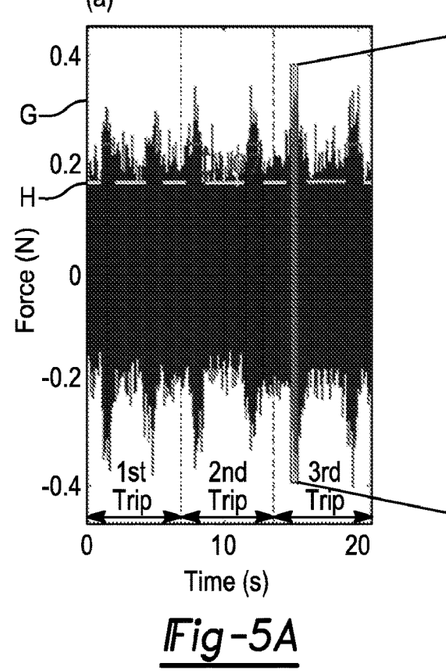
FIGS. 5A-5B are graphs illustrating the force measurement and plaque grinding force.

FIG. 5A shows the measured force during RA. Six peaks indicate the elevated force during plaque grinding when the burr axially passed though the plaque surrogate. The average magnitude of the plaque grinding force, G, illustrated by the marker in FIG. 5A, was 0.23 N. The force magnitude in vessel phantom, H, was 0.07 N smaller than that in the bone, as shown in FIG. 5A. The force in grinding the vessel phantom is mainly due to the elastohydrodynamic film generated between the burr and the soft PVC.

Figure 5B:
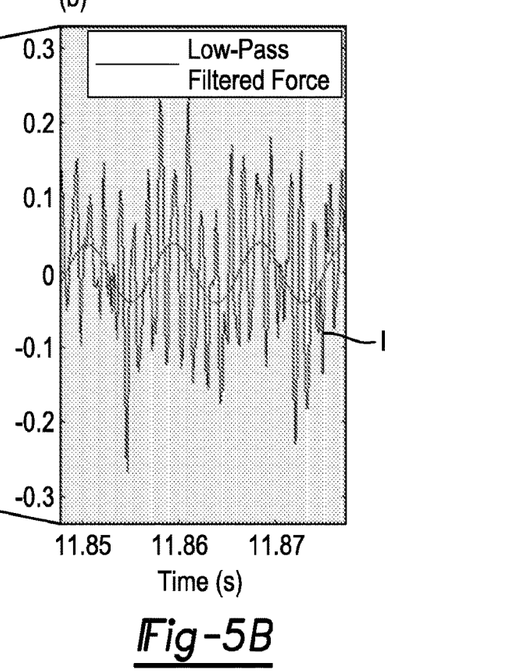

A close-up view of 0.03 s of the plaque grinding force is shown FIG. 5B. A low pass filter with a 200 Hz cut-off frequency is applied. The filtered data, I, in FIG. 5(b), shows a sinusoidal wave. The dominant frequency matches the burr orbital frequency of burr motion observed by the high-speed camera.

Discrete Grinding

Figure 6A:
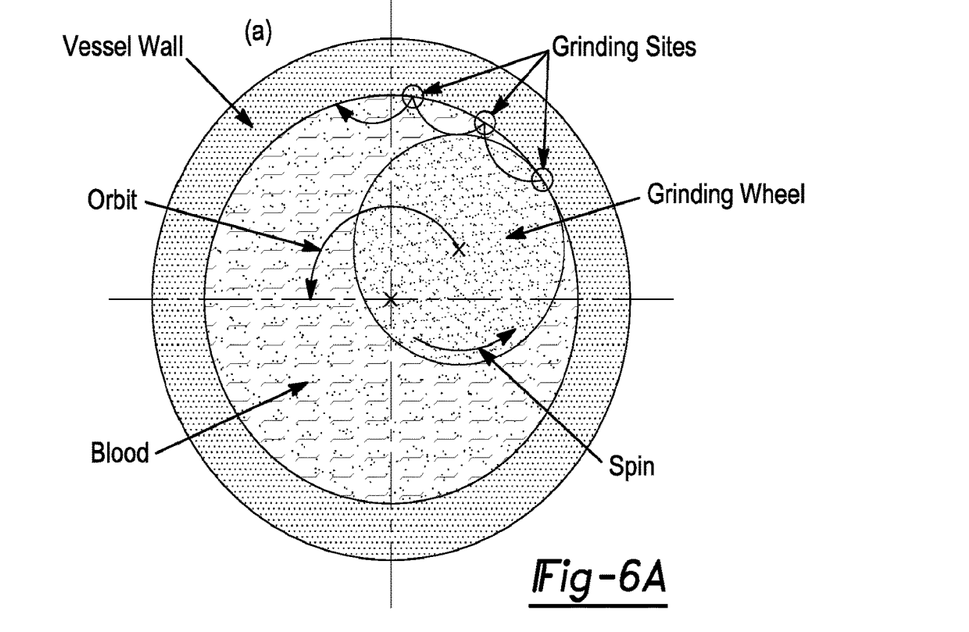
FIGS. 6A-6B show discrete grinding mechanism and ground surface.
Figure 6B:
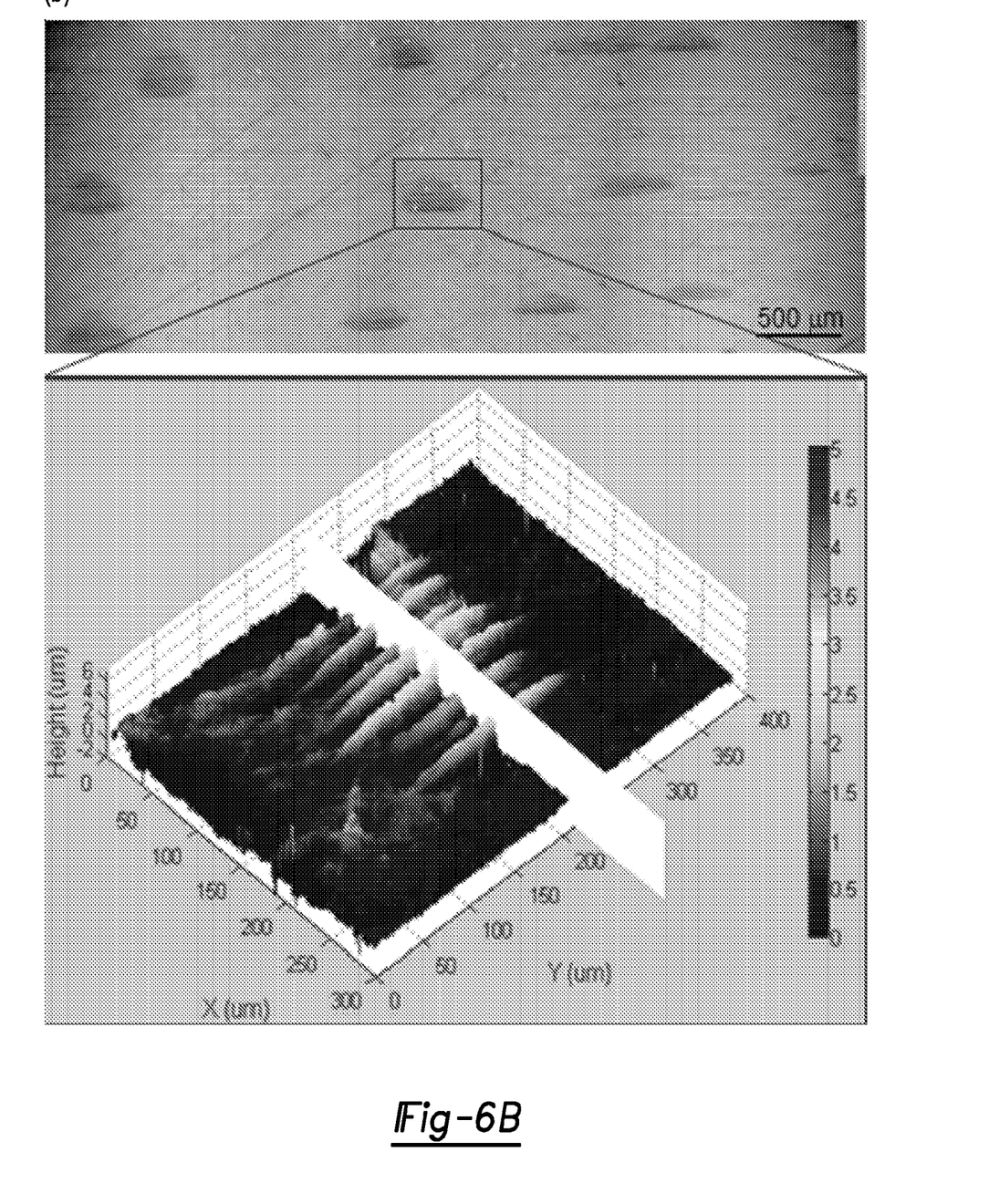

A discrete grinding mechanism was observed as shown in FIG. 6A, while orbiting the grinding wheel bounces near the wall resulting in discrete grinding sites. These sites were examined on the ground surface by environmental scanning electron microscopy as shown in FIG. 6B. A single grinding site was imaged by laser confocal scanning and showed multiple grooves cut by the abrasives.

This process was caused by the blood hydraulic, grinding, and centrifugal forces and the drive shaft flexibility. The blood hydraulic force induced by the wheel rotation pushes the grinding wheel to the artery wall. When the wheel contacts the artery wall, the cutting force overcomes the hydraulic force pushing the wheel off the wall. The orbital centrifugal force then takes over and presses the wheel to the wall again. Increasing orbital speed generates large centrifugal force for the grinding wheel to impact the artery wall.

Debris Size in RA

Figure 7:
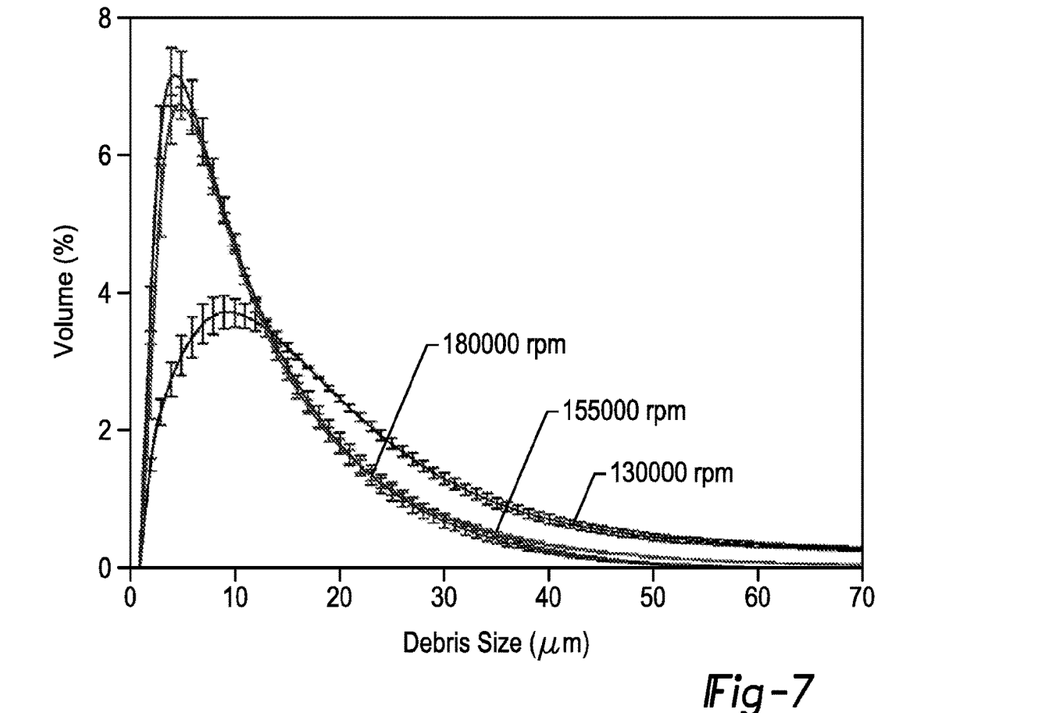
FIG. 7 is a graph illustrating the debris size distributions for 130,000, 155,000 and 180,000 rpm.

FIG. 7 shows the average and three standard deviation of the debris size distribution under 130,000, 155,000, and 180,000 rpm rotational speeds. With the rotational speed increasing, the size distribution curve becomes narrower. 90% of the debris is less than 45, 31, and 25 μm at 130,000, 155,000, and 180,000 rpm, respectively. Higher rotational wheel results in smaller debris size.

Catheter Temperature

Figure 8:
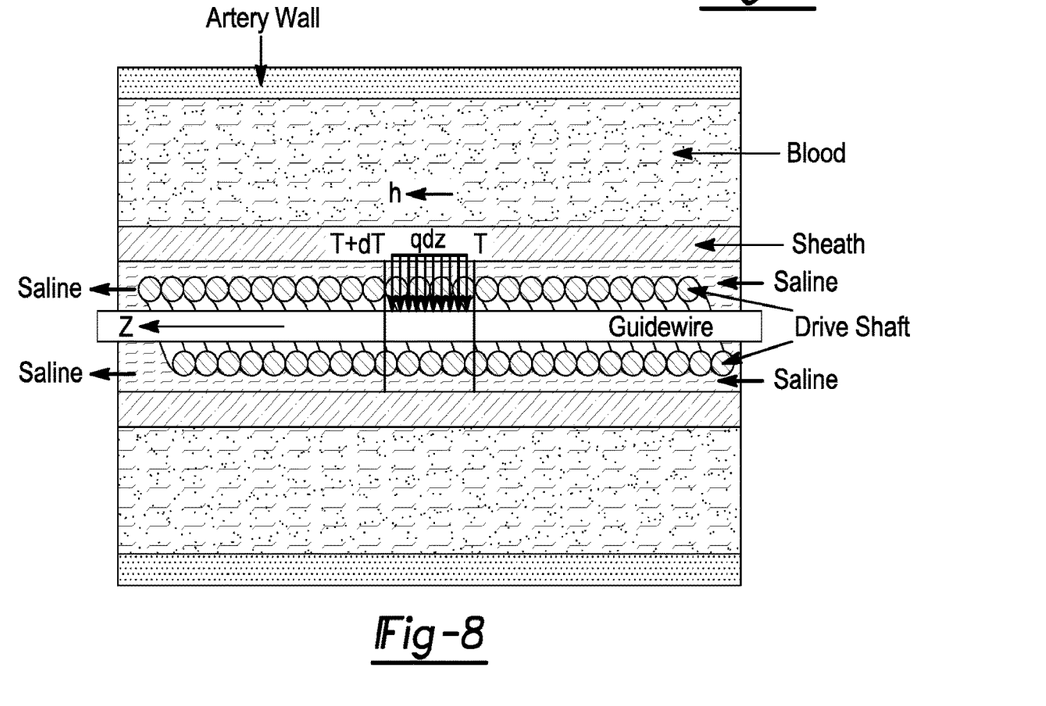
FIG. 8 is a schematic of the catheter thermal model.

The schematic of the heat transfer was presented in FIG. 8. Friction on the rotational drive shaft between the guidewire and the plastic sheath generates heat absorbed by the saline flow, resulting in a temperature rise of the catheter and saline. As the sheath length is much larger than the inside radius of cross-section, temperature variations in the radial and azimuthal directions are assumed to be negligible. A 1-D advection—diffusion model with constant heat source is chosen to study this process. The solution to this model is as follows:

$$T = \sum a_n e^{-\left(\frac{k}{\rho c}(n\lambda)^2 + \frac{h}{\rho p c}\right)t} \cos(2n\lambda(z - v_z t)) + \frac{qp}{h}\left(1 - e^{-\frac{h}{\rho p c}t}\right) + T_o$$

where ρ is the density of saline water, c is the specific heat at constant pressure, k is the thermal conductivity, q is the constant heat flux generated by the friction of the rotational drive shaft against the stationary guidewire and sheath. $p=2\pi r$, r is the outside diameter of the catheter, $a_n$, b, and c are constant, λ is systematical constant, and $T_o$ is the initial temperature of saline water.

Experiments were conducted to decide the system constants. With this model the effects of the rotational speed, saline flow rate, blood flow rate, insertion length (RSBI) were presented in the Table 1. Tissue thermal damage may occur when the rotational speed is high and blood flow rate is small as demonstrated in cases 5, 7, 8, and 9 in Table. 1.

TABLE 1

RSBI effects on the saline temperature.

| | Experimental design R-S-B-I (krpm-ml/min-ml/min-m) | Heat flux ($10^6$ W/m$^2$) | Temperature rise at sheath endpoint (° C.) | Temperature at saline water (° C.) |
|---|---|---|---|---|
| 1 | 135-12-40-0.3 | 2.32 | 2.65 | 4.55 |
| 2 | 135-8-20-0.5 | 2.34 | 3.49 | 4.32 |
| 3 | 135-4-0-0.7 | 2.24 | 3.50 | 3.60 |
| 4 | 155-12-20-0.7 | 3.16 | 4.16 | 4.77 |
| 5 | 155-8-0-0.3 | 3.37 | 6.15 | 8.05 |
| 6 | 155-4-40-0.5 | 3.2 | 2.23 | 3.75 |
| 7 | 175-12-0-0.5 | 4.7 | 8.26 | 10.04 |
| 8 | 175-8-40-0.7 | 4.65 | 4.92 | 6.43 |
| 9 | 175-4-20-0.3 | 4.11 | 5.17 | 8.16 |

According to the principles of the present teachings, a two-phase atherectomy technique is provided using an axisymmetric device that permits a physician or a surgeon to restore the artery patency with minimized cutting force and collateral temperature rise. In some embodiments, new designs of the grinding wheel and a catheter temperature control system are provided to avoid tissue thermal damage and blood coagulation.

Two-Phase Atherectomy

In some embodiments, the two-phase atherectomy technique of the present teachings comprise a phase (1) low-speed rotational drilling step and phase (2) high-speed orbital impact resulting in plaque micro-fractures.

Figure 9A:
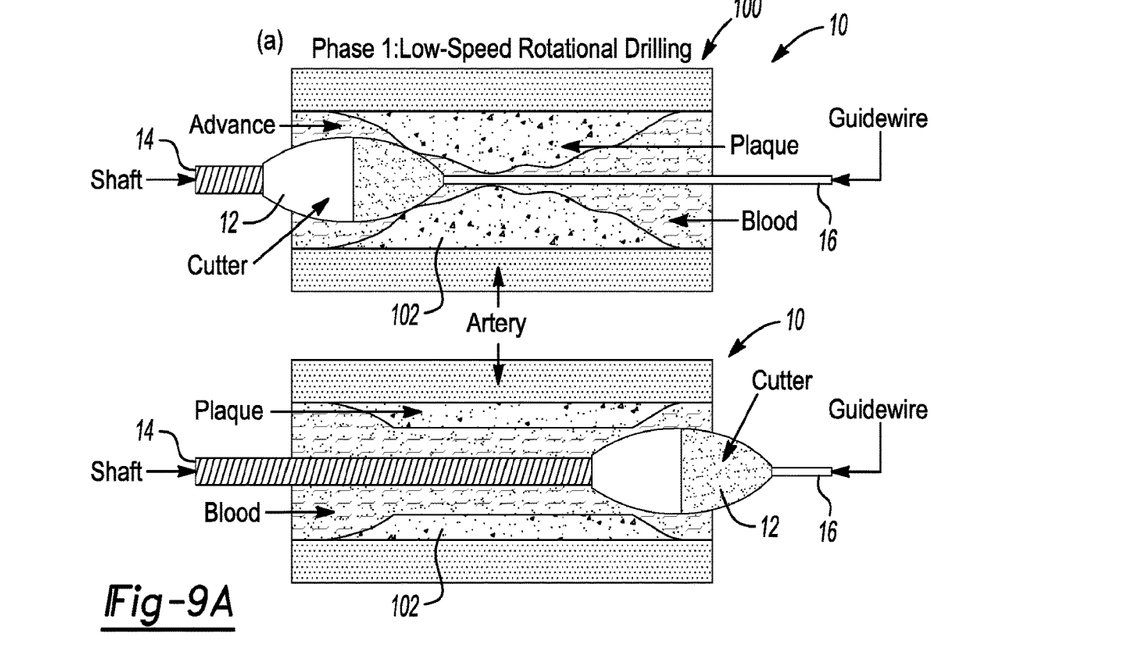
FIGS. 9A-9B are schematics of a two-phase atherectomy technique and device according to the principles of the present teachings.

During Phase I, when the lesion lumen size is smaller than the cutter, as shown in the FIG. 9A, a rotating cutter 12 advances through the stenosis 100 and cuts the plaque 102 off as a drill bit to create a channel 12 of the cutter size. The cutter 12 is rotationally supported by a shaft 14 that imparts a rotational force upon cutter 12 such that the cutter 12 rotates about a rotational axis of the shaft 14. This rotational axis is generally stationary during Phase I. A guide wire 16 may extend from a forward end 18 of cutter 12 to urge cutter 12 and shaft 14 along an artery or other tubular member 110. This process involves a large contact area between the cutter 12 and plaque 102 which tends to cause high cutting force and temperature. Low cutter rotational speed is required to avoid tissue damage. By way of non-limiting example, low cutter rotational speed is generally regarded as being in the range of about 90,000 to 170,000 revolutions per minute. In some embodiments, low cutter rotational speed of 135,000 revolutions per minute has been found to be desirable.

Figure 9B:
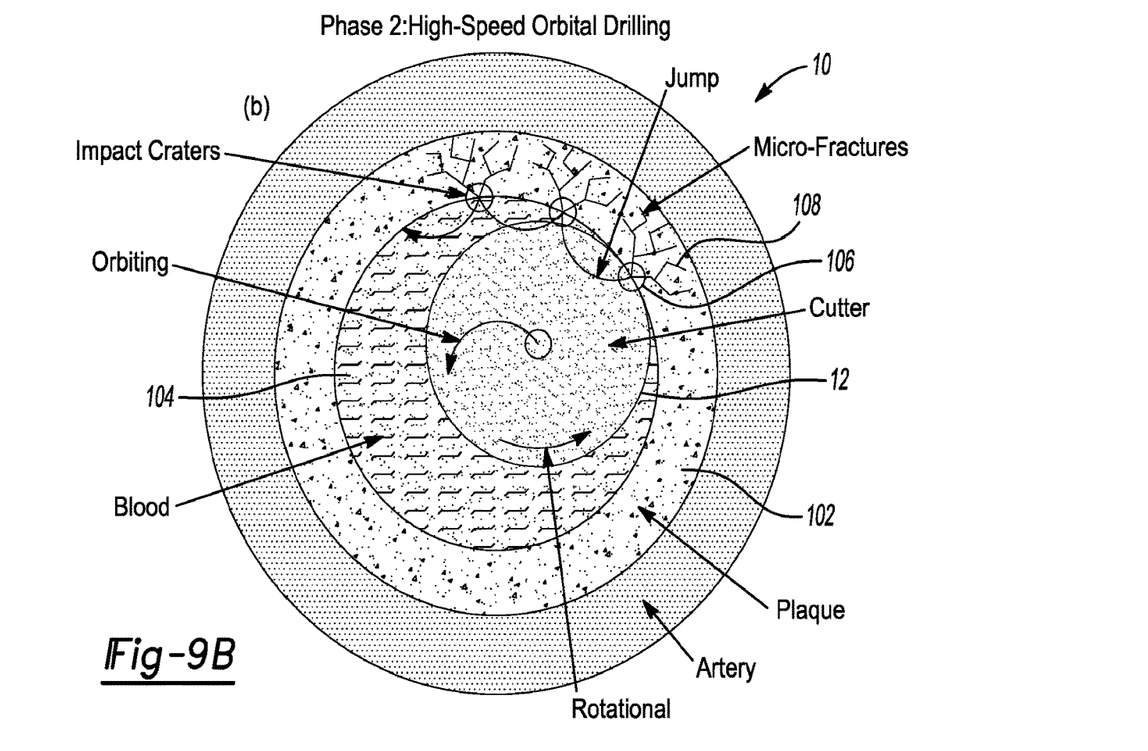

When the lumen size 104 is enlarged to allow the cutter translation in the radial direction as demonstrated in FIG. 9B, the cutter orbits around the vessel due to blood fluid mechanics during Phase II. While orbiting, the cutter 12 continues to rotate about the rotational axis of Phase I, but the cutter 12 and the associated rotational axis further adopts or defines an orbital motion whereby the rotational axis begins to generally orbitally rotate within the artery. The cutter 12 thus hits the plaque 102, bounces up or away due to the cutting/impact force, and is pushed to hit the plaque 102 again by the centrifugal force. This process generates impact crater points 106 and cracks 108 in the plaque 102, further enlarging the lumen 104 and disrupting the plaque tissue 102 to restore artery patency and elasticity. The orbital and jumping motion are dominated by the orbital centrifugal force. To increase the orbital speed and impact force, high cutter rotational speed is recommended, as derived from our cutter motion study. By way of non-limiting example, high cutter rotational speed is generally regarded as being in the range of about 170,000 to 250,000 revolutions per minute. In some embodiments, high cutter rotational speed of 185,000 revolutions per minute has been found to be desirable. As higher speeds are associated with a higher temperature and increased risk of blood coagulation and thermal injury, temperature control during atherectomy is imperative.

Figure 10:
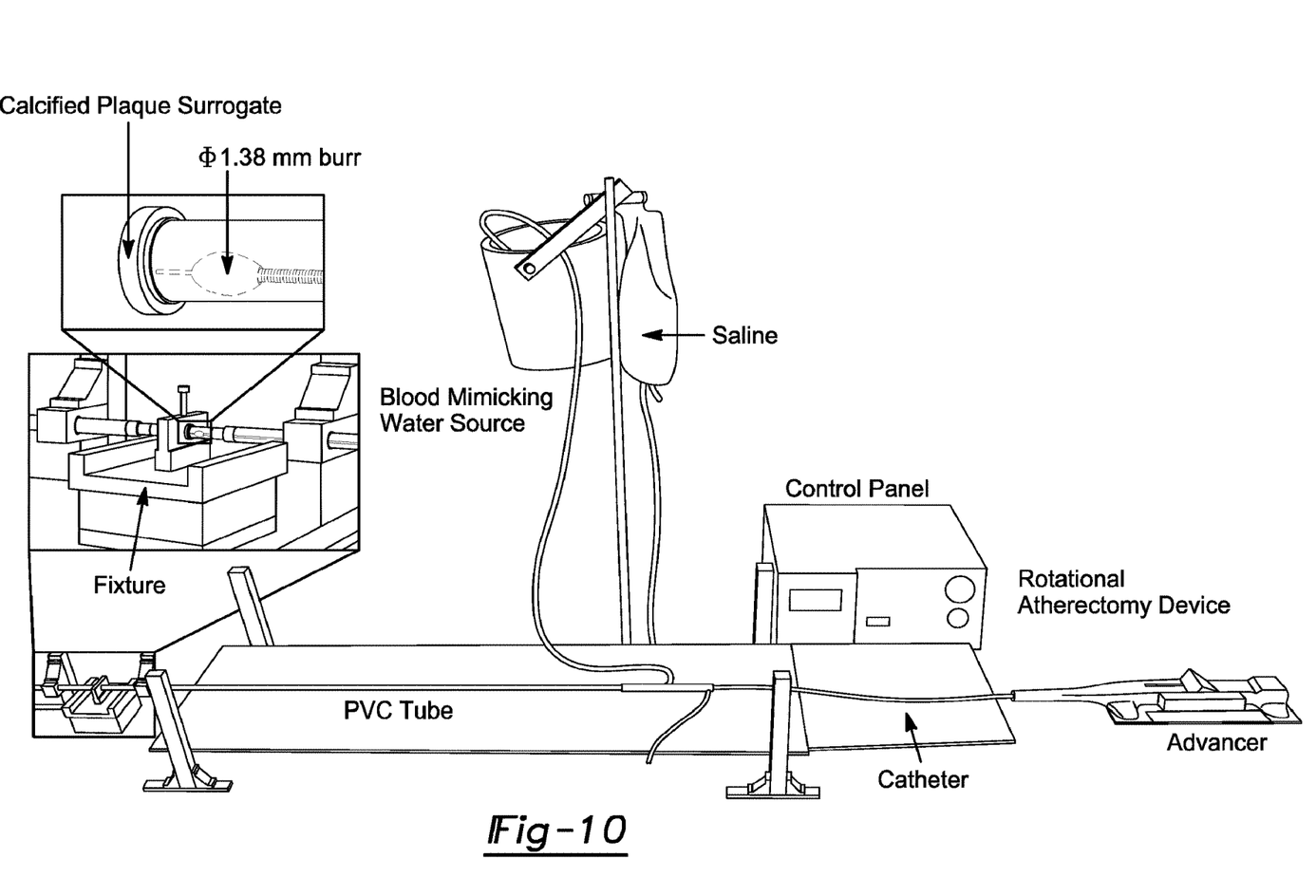
FIG. 10 is a photograph illustrating the experimental setup of the two-phase atherectomy technique in terms of the luminal gain.

An experiment has been conducted to show the efficacy of the two-phase atherectomy technique in terms of the luminal gain. The experimental setup, as shown in FIG. 10, consists of the rotational atherectomy device 10 with a 1.38 mm diameter burr 12, a PVC tube with water flowing through to mimic the artery 110, and a surrogate to the calcified plaque 102.

Figure 11A:
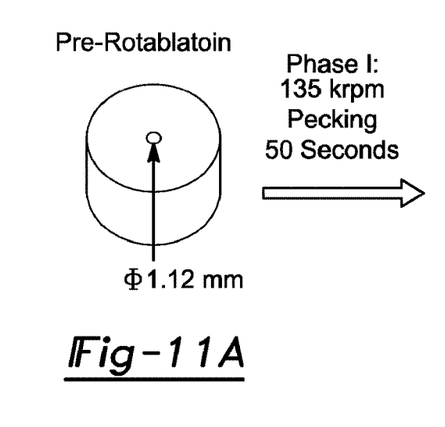
FIG. 11A shows two-phase atherectomy and results with calcified plaque surrogate before rotablation.

The calcified plaque surrogate was made from Ultracal 30 plaster with a 1.12 mm diameter hole as shown in FIG. 11A. The surrogate was fixed in a fixture and connected to the PVC tube to allow water flowing through the surrogate. The catheter of the device was inserted into the PVC tube with the guidewire 16 passing through the lumen of the surrogate and grinding wheel 12 locating near the surrogate.

The test started from Phase I with the burr rotating at 135,000 rpm and drilling through the surrogate with a pecking motion (moving forward to engage the surrogate for a short period and backward to disengage, then forward again to reengage, and repeating the process). During the burr advancement, the rotational speed was maintained higher than 130,000 rpm. It took 50 seconds to drill through the surrogate and finish Phase I. A 1.43 mm diameter lumen, slightly larger than the burr 12, was obtained from Phase I, as shown in FIG. 11B.

Once the burr drilled through the surrogate, Phase II technique was implemented by increasing the burr rotational speed to 185,000 rpm and moving the burr 12 back and forth through the surrogate. Phase II lasted 100 seconds, during which no drop of rotational speed was observed. Phase II generated a 2.72 mm diameter lumen, which was almost twice larger than the 1.38 mm burr, because of the burr orbital motion.

Figure 11B:
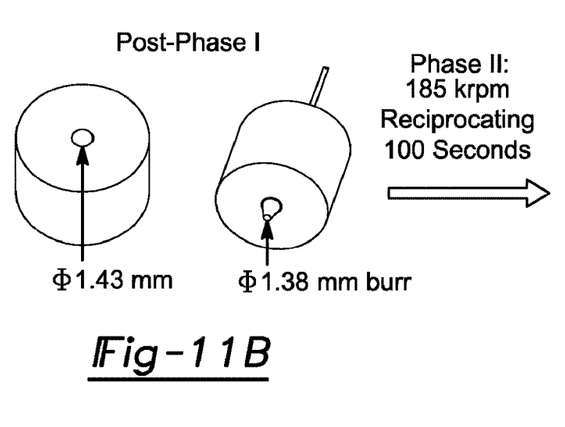
FIG. 11B shows two-phase atherectomy and results with 1.43 mm diameter lumen obtained from Phase I.
Figure 11C:
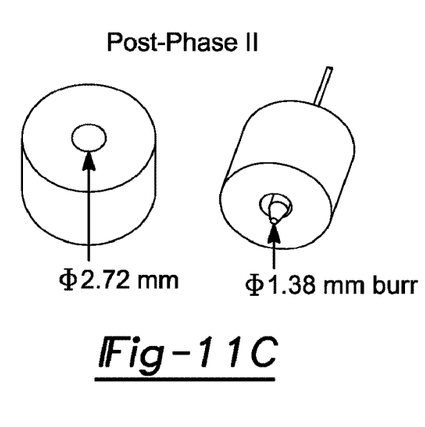
FIG. 11C shows two-phase atherectomy and results with the resultant 2.72 mm diameter lumen after Phase II.

As summarized in FIG. 11, with the two-phase atherectomy technique of the present teachings, using a single 1.38 mm burr, a 2.72 mm lumen was obtained from a 1.12 mm diameter lumen, which proves the efficacy of the two-phase atherectomy.

This approach will allow an operator using the axisymmetric atherectomy device of the present teachings to achieve some of the advantages of the orbital atherectomy system without incurring the disadvantages that are inherent to a dedicated orbital atherectomy device In the first embodiment, the approach can be used with the pre-existing rotational atherectomy device.

Figures 12A, 12B:
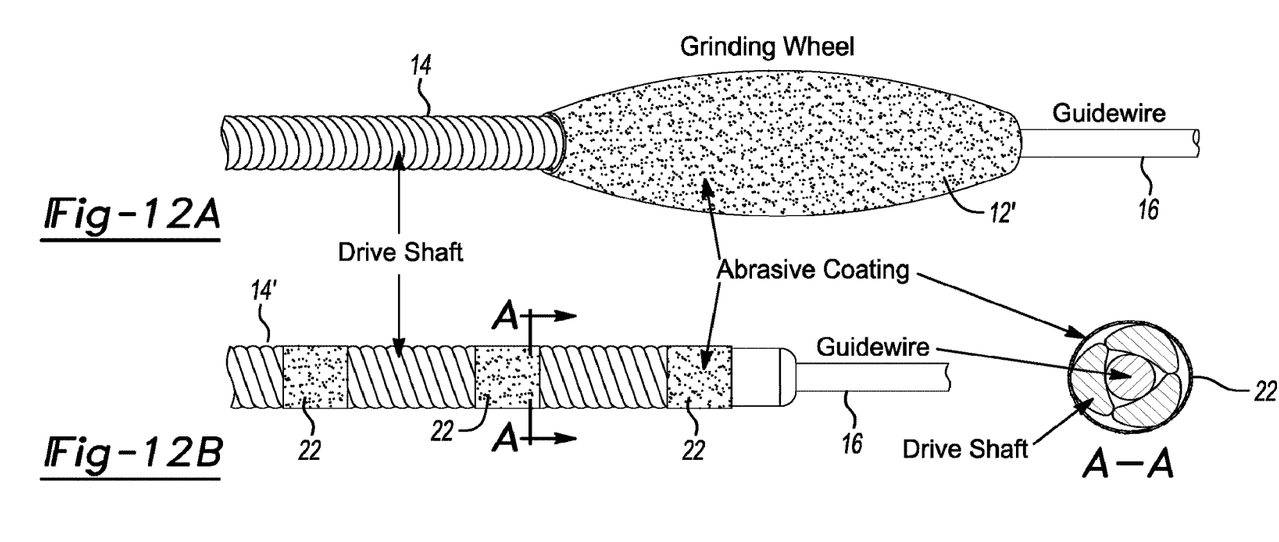
FIG. 12A illustrates the grinding wheel design for two-phase atherectomy with a fusiform grinding wheel.
FIG. 12B illustrates the grinding wheel design for two-phase atherectomy with a micro flexible grinding wheel.

We also propose additional embodiments that will allow further enhancements to the technique Grinding Wheel Design for Two-Phase Atherectomy To facilitate the two-phase atherectomy technique, we propose an axial-symmetric fusiform grinding wheel and a micro-shaft based flexible grinding wheel, as shown in FIGS. 12A and 12B.

Embodiment: Fusiform Grinding Wheel

FIG. 12A shows the fusiform grinding wheel 12' with diamond abrasives coating 20 on the entire wheel surface, different from the burr used in RA which has only the distal half coated with abrasives (FIG. 1A). This design can enhance Phase II of the two-phase atherectomy when the grinding wheel reciprocates through the lesion while orbiting, removing plaque during both forward and backward motions. This would also minimize the risk of the device entrapment—a rare but life threatening problem that is associated with the current RA device Embodiment: Micro Flexible Grinding Wheel FIG. 12B illustrates the micro flexible grinding wheel design. Discrete sections of the drive shaft 14' are coated with abrasives 22. This discrete band coating 22 keeps the flexibility of the coiled drive shaft 14', allowing the grinding wheel to be navigated through tortuous lesion. The abrasive coating 22 is about 100 μm thick, making the grinding wheel sub-millimeter in size (the diameter of current drive shaft in RA is 0.65 mm), which makes this grinding wheel suitable for small vessels.

Figure 13:
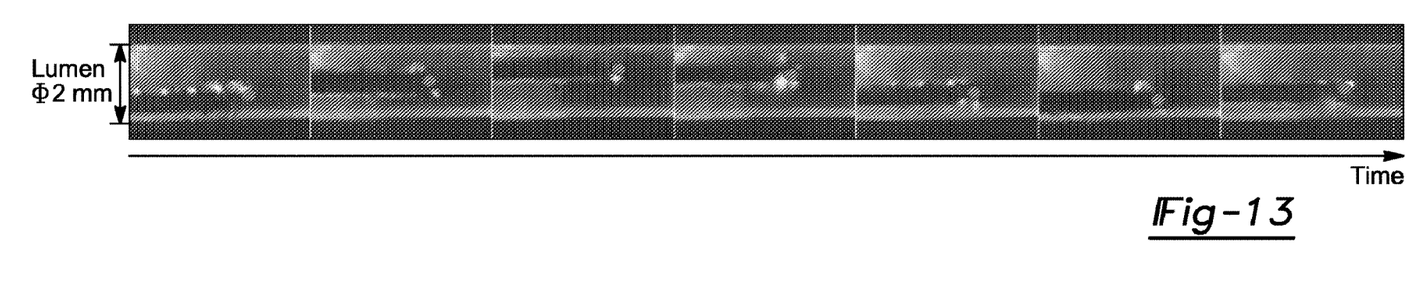
FIG. 13 shows the orbital motion of the micro flexible grinding wheel rotating at 135,000 rpm in a 2 mm diameter vessel phantom.

To demonstrate the feasibility of this drive shaft based micro grinding wheel in two-phase atherectomy, an experiment has been conducted to observe the orbital motion of the micro grinding wheel in a small (2 mm) vessel phantom using high-speed camera. FIG. 13 shows seven frames over time in an orbital period of the grinding wheel with the red dots indicating the locations of the tip of the grinding wheel. Such a device may be particularly suitable for small vessels and along vessels with turns and tortuosity Catheter Temperature Control System Catheter temperature control system 30 comprises a sheath 32 with a temperature sensor 34 and a temperature regulator 36. The sheath 32 is a plastic tube in which drive shaft 14 rotates and saline or special biologically compatible lubricating fluid 38 flows. The shaft rotation on the guidewire generates heat. Saline (or other lubricant) flows to cool and lubricate the drive shaft.

Embodiment

Figure 14:
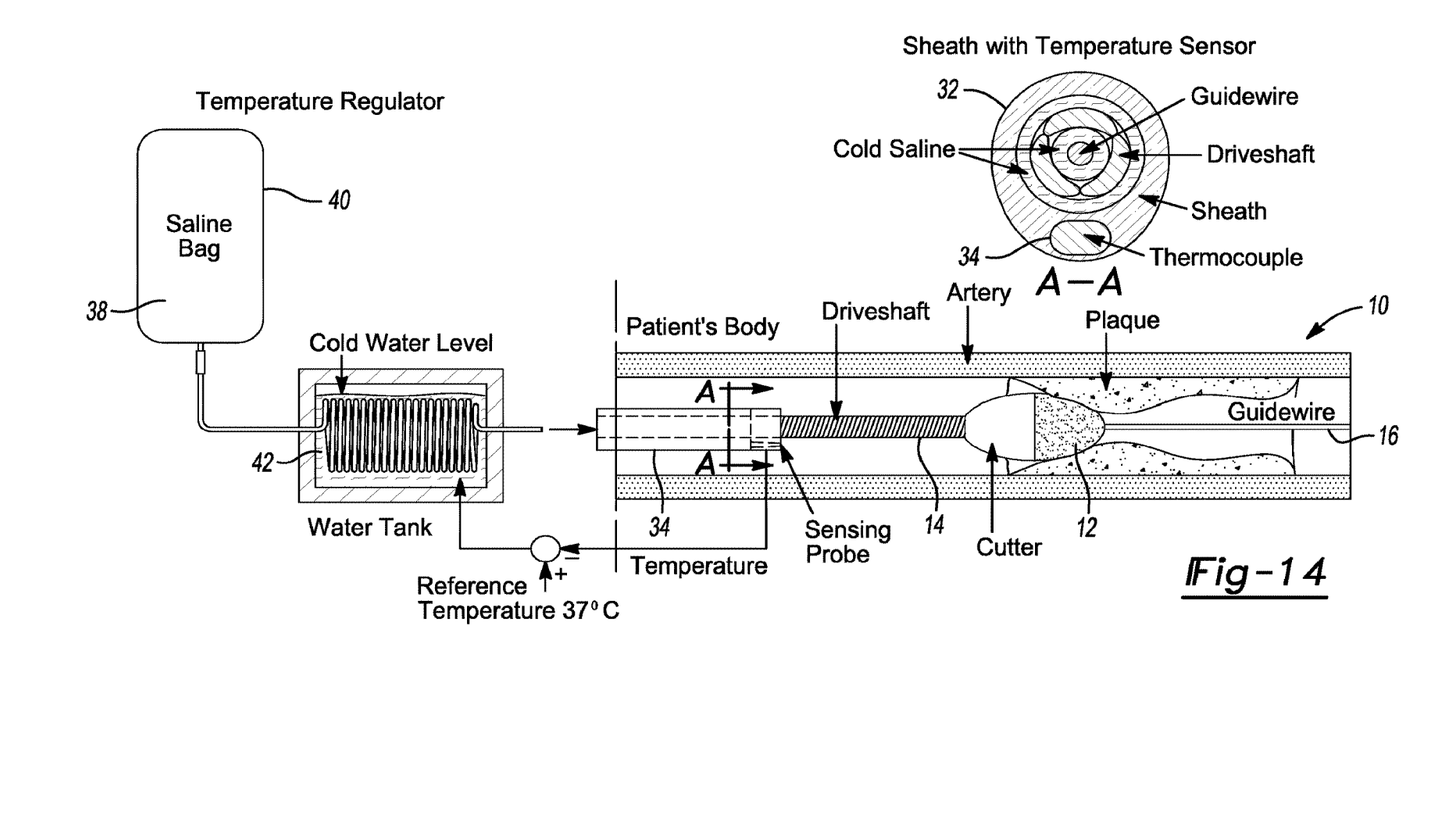
FIG. 14 is a schematic of a catheter temperature control system.

The temperature sensor 34, a thermocouple, is imbedded in the wall of the sheath 32 along the catheter with the sensing probe locating near the treatment site as shown in the FIG. 14. Real-time temperature during atherectomy is measured as the feedback signal to the temperature regulator. The regulator controls the lesion temperature by adjusting the level of cold water in a tank 40 where saline 38 flows through a section of coiled tube 42. When the cold water level rises, contact area for heat exchange between the cold water and the coiled tube increases and the saline temperature drops.

In another embodiment of the device, there is no thermocouple 34 but based on the rotational velocity elected for use, the temperature rise is estimated and the lubricant is cooled to a temperature sufficient to neutralize the heat generated in the catheter and prevent thermal injury to the vessel wall or to the flowing cells, proteins and other constituents of blood in the vessel. In this embodiment, as the rotational speed is adjusted, this will trigger a change in the temperature of the coolant and thus of the lubricant and reduce tissue injury.

An experiment has been conducted to prove the concept of the temperature control system. As reported in Table 1, when grinding wheel rotated at 175,000 in an occluded lesion (no blood flow) with 24° C. (current atherectomy procedure uses room temperature saline) saline delivered at 12 ml/min, the temperature rise of the treatment region was 10° C. which will cause tissue thermal damage. Keep the same experiment condition, when the saline was cooled to 9° C., the temperature rise in the lesion was reduced to 1.8° C., which shows the feasibility of using our proposed temperature control system to avoid tissue thermal damage in atherectomy.

Applications

The clinical utility of this device would be to use one device to create a large lumen than has been previously assumed possible and modify the current technique of rotational atherectomy that has been focused on using devices in a sequential fashion of increasing sizes until the appropriate lumen size is achieved. The two-phase atherectomy will allow the use of a single device to achieve a lumen larger than the device with the drilling phase (Phase I) creating a lumen that is either large enough to permit enough blood flow for relief of symptoms or for delivery of other interventional devices (especially drug eluting balloons or stents). The impact phase of the device (Phase II) is used to create micro-fractures in the plaque that then make the calcified plaque suitable for further intervention by high pressure balloon angioplasty or stenting and would respond appropriately to such devices or would be enough to create a larger lumen by itself. Thus the device would be used to prepare the lesion prior to stenting or as the sole treatment. This phase could also be applied for treatment of lesions where a stent is deployed but fails to fully expand and thus is at high risk for thrombosis and restenosis. The ability of the device to induce micro-fractures could thus be applied inside an incompletely expanded stent where the force transmitted at the impact craters could create plaque fissure points that could subsequently be expanded using a high pressure balloon or another device.

The technique and device here introduced are suitable for 1) rotational atherectomy, 2) orbital atherectomy, and 3) temperature sensitive catheter based surgery.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of two-phase atherectomy for removal of plaque within an artery forming a stenosis, the method comprising:
   a first phase of rotational drilling by exerting a rotational force on a cutter to form a channel within the plaque having a diameter substantially equal to a diameter of the cutter, the cutter being rotated at a first rotational speed sufficient to maintain rotation of the cutter about a rotational axis, wherein the rotational axis is stationary during the first phase; and
   a second phase of orbital impact by exerting a rotational force on the cutter to result in radial orbital motion of the cutter within the channel resulting in periodic impact of the cutter upon the plaque to form micro-fractures within the plaque and enlarge the diameter of the channel to a diameter substantially greater than the diameter of the cutter, the cutter being rotated at a second rotational speed sufficient to result in the radial orbital motion of the cutter such that the rotational axis of the cutter generally orbits an orbital axis, the rotational axis being offset from the orbital axis.

2. The method according to claim 1 wherein the radial orbital motion of the second phase is due to fluid mechanics within the artery.

3. The method according to claim 1 wherein the periodic impact of the cutter upon the plaque comprises the cutter hitting the plaque, bouncing away from the plaque due to the impact force, and then hitting the plaque again due to centrifugal force.

4. The method according to claim 1 wherein the first rotational speed is in the range of about 90,000 to about 170,000 revolutions per minute.

5. The method according to claim 1 wherein the first rotational speed is about 135,000 revolutions per minute about the rotational axis.

6. The method according to claim 1 wherein the second rotational speed is in the range of about 170,000 to about 250,000 revolutions per minute.

7. The method according to claim 1 wherein the second rotational speed is about 185,000 revolutions per minute about the rotational axis.

8. The method according to claim 1 wherein the first phase of rotational drilling further comprises a pecking motion being a periodic engagement and disengagement of the cutter with the plaque.

9. The method according to claim 1 further comprising:
   monitoring a temperature of at least one of the cutter, a guidewire, a drive shaft, and a sheath; and
   introducing a fluid within at least one of the sheath and the artery during at least one of the first phase and the second phase.

10. The method according to claim 9 wherein the monitoring a temperature comprises disposing a temperature sensor within the sheath and providing a temperature regulator introducing the fluid.

11. The method according to claim 1 wherein the cutter comprises an abrasive coating disposed on both a leading face and a trailing face thereof.

12. The method according to claim 1 wherein the cutter comprises a plurality of discrete abrasive sections disposed along a shaft thereof.

13. The method according to claim 12 wherein each of the plurality of discrete abrasive sections is about 100 μm thick.

* * * * *